United States Patent [19]

Voll et al.

[11] Patent Number: 4,996,887

[45] Date of Patent: Mar. 5, 1991

[54] DEVICE FOR TAKING SAMPLES OF BOTTOM SEDIMENTS AND BOTTOM WATER FROM WATER BASINS

[76] Inventors: Martin A. Voll, Kharri I. Yankovsky, Robert K. Eiskop, all of Tallin, U.S.S.R.

[73] Assignee: Institut Khimii Akademii Nauk, Tallin, U.S.S.R.

[21] Appl. No.: 403,923

[22] Filed: Sep. 7, 1989

[51] Int. Cl.$^5$ .......................... G01N 1/08; G01N 1/12
[52] U.S. Cl. .............................. 73/864.44; 73/170 A; 175/59
[58] Field of Search .......... 73/864.44, 864.45, 170 A, 73/864.63; 175/58, 59, 60

[56] References Cited

U.S. PATENT DOCUMENTS

| | | | |
|---|---|---|---|
| 2,753,717 | 7/1956 | Obrcian | 73/864.44 X |
| 3,345,879 | 10/1967 | Nasu et al. | 73/170 A X |
| 3,915,245 | 10/1975 | Tuccillo | 175/58 X |
| 4,234,046 | 11/1980 | Haynes | 175/58 X |
| 4,317,490 | 3/1982 | Milberger et al. | 175/59 X |
| 4,709,584 | 12/1987 | Voll et al. | 73/864.44 |
| 4,807,707 | 2/1989 | Handley et al. | 73/864.74 X |
| 4,838,079 | 6/1989 | Harvi | 73/863.33 X |

FOREIGN PATENT DOCUMENTS

| | | | |
|---|---|---|---|
| 1419025 | 10/1965 | France | 73/864.44 |
| 294091 | 6/1971 | U.S.S.R. | 73/170 A |
| 542930 | 2/1977 | U.S.S.R. | 73/170 A |
| 544886 | 2/1977 | U.S.S.R. | 73/170 A |
| 626384 | 9/1978 | U.S.S.R. | 73/170 A |
| 637620 | 12/1978 | U.S.S.R. | |
| 800785 | 2/1981 | U.S.S.R. | 73/170 A |
| 1013810 | 4/1983 | U.S.S.R. | |

*Primary Examiner*—Tom Noland
*Attorney, Agent, or Firm*—Fleit, Jacobson, Cohn, Price, Holman & Stern

[57] ABSTRACT

A device for taking samples of bottom sediments and bottom water from water basins comprises at least one vertical sectional coring tube having a closed upper end provided with a check valve. On the upper end of the coring tube a bathometer is secured so that the upper end of the coring tube is at the same time the lower end of the bathometer. The bathometer has in its upper end a check valve, a means in the upper part for intake of air and a means in the lower part for release of bottom water. The coring tube is secured by its upper end to the carrying element.

2 Claims, 1 Drawing Sheet

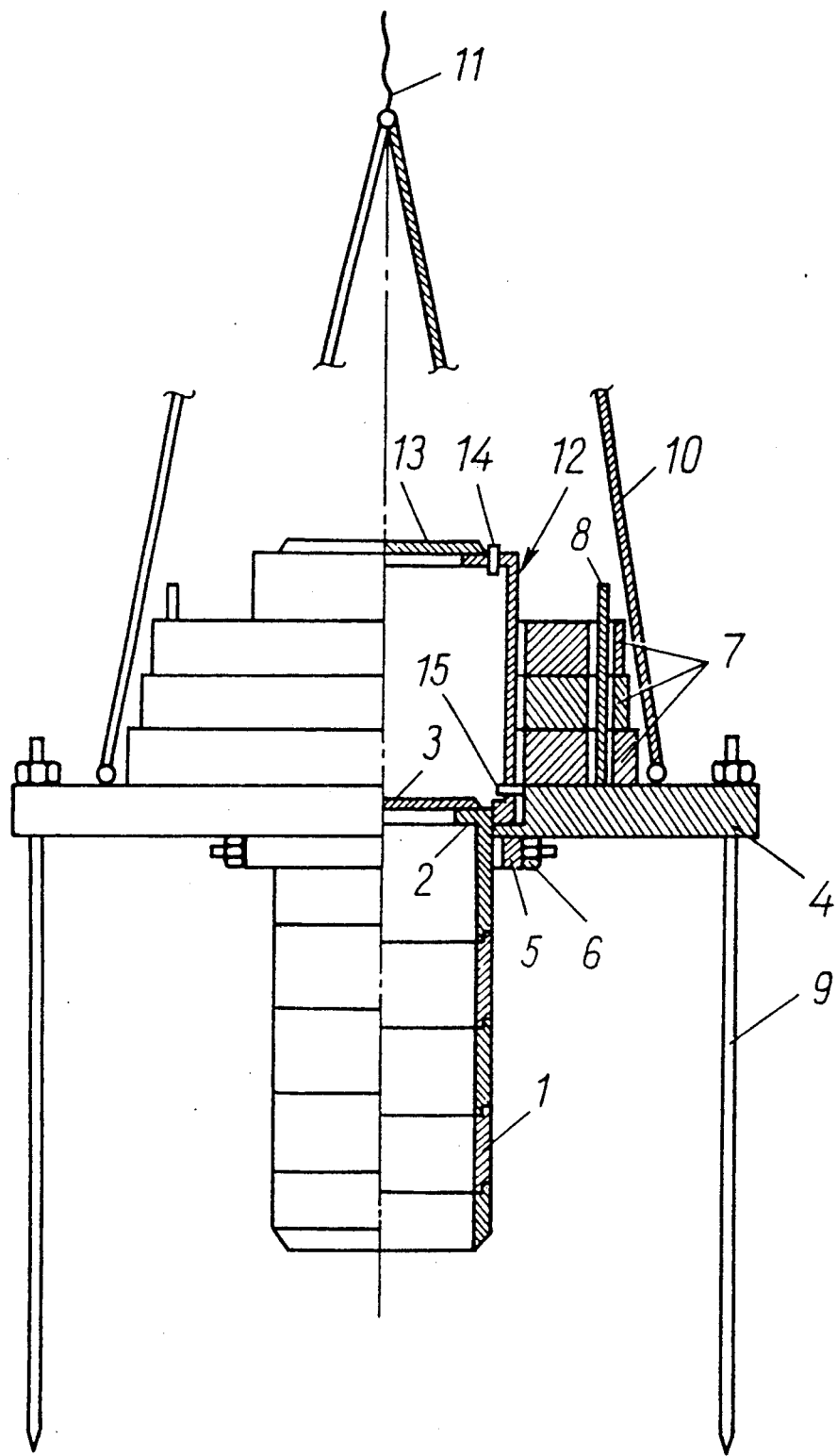

DEVICE FOR TAKING SAMPLES OF BOTTOM SEDIMENTS AND BOTTOM WATER FROM WATER BASINS

FIELD OF THE INVENTION

The invention relates to the oceanographic instruments for investigating properties of substances and, more particularly, to devices for taking samples of bottom sediments and bottom water from water basins.

BACKGROUND OF THE INVENTION

Known in the prior art is a device for taking samples of bottom sediments from water basins, comprising a vertical sectional coring tube having a closed upper end provided with a check valve, a ballast weight on the upper end of the coring tube and the side stationary supports (cf. USSR Inventor's Certificate No. 1,013,810, class G01N 1/10, published in 1983).

This device, however, makes it impossible to take the samples of bottom water.

Also known in the prior art is a device for taking sample of bottom sediments and bottom water, comprising a coring tube and bathometers (cf. USSR Inventor's Certificate No. 637,620, class G1N 1/10, published 1978).

In the known device the bathometers are attached to the frame having a base, to which by means of the studs also the coring tube is connected. The device takes samples of sediments and water, but as the coring tube and bathometers are placed separately, this device makes it impossible to take the same of bottom sediments together with the sample of bottom water, being in direct contact with the bottom sediments.

The invention is aimed at elaborating a device for taking samples of bottom sediments and bottom water with such a construction that enables us to take together with the samples of bottom sediments also the sample of water, being in direct contact with the bottom sediments.

SUMMARY OF THE INVENTION

It is an object of the invention to obtain a reliable data on the nature of the bottom sediments and water being in direct contact with the bottom sediments.

The nature of the invention consists in that in a device for taking samples of bottom sediments and bottom water, comprising a vertical coring tube and a bathometer, according to the invention the coring tube has a closed upper end provided with a check valve, on said upper end the bathometer is secured so that the upper end of the coring tube is at the same time the lower end of the bathometer, and the bathometer has in its closed upper end a check valve, a means (for example, a valve, a stopcock, etc.) in its upper part for intake of air and a means (for example, a valve, a stopcock, etc.) in its lower part for release of bottom water. The coring tube is secured by its upper end to the carrying element. To enable us to take parallel samples the device may comprise more than one coring tube and more than one bathometer.

It is desirable that the device for taking samples of bottom sediments and bottom water should be provided with at least three supports having upper and lower ends and the length of the coring tube, placed uniformly around the coring tube and secured by their upper ends to the carrying element.

The device for taking samples of bottom sediments and bottom water from water basins, worked out according to the present invention, enables simultaneous taking of the samples of bottom sediments and the sample of water, being in direct contact with the bottom sediments. This is particularly important for investigating the mechanism of mass transfer from the water phase into the bottom sediments and vice versa. The device is of simple design and features high reliability.

BRIEF DESCRIPTION OF THE DRAWINGS

The invention will now be described in greater detail with reference to specific embodiments thereof, taken in conjunction with the accompanying drawing, wherein according to the invention, the device for taking samples of bottom sediments and bottom water from water basins is illustrated, partly in section.

DETAILED DESCRIPTION OF THE INVENTION

The device, illustrated in the drawing, comprises a vertical sectional coring tube 1 having a closed upper end 2 provided with a check valve 3, a carrying element 4, being at the same time the main ballast weight, to which by means of a strip 5 and bolts 6 by its upper end 2 the coring tube 1 is secured, an additional ballast weight 7 consisting of a set of removable disks installed of uprights 8, supports 9, at least three in quantity, having the length exceeding the length of the coring tube 1, placed uniformly around the tube 1 and secured by their upper ends to the carrying element 4, bars 10, by means of which the device is suspended to a rope 11. On the upper end 2 of the coring tube 1 a bathometer 12 is secured so that the upper end 2 of the coring tube 1, provided with a check valve 3, is at the same time the lower end of the bathometer 12. The bathometer 12 has in its closed upper end a check valve 13 similar to the check valve 3. In its upper part it has also a means 14, for example, a valve, for intake of air, and in its lower part a means 15, for example, a valve, for release of bottom water.

The device for taking samples of bottom sediments and bottom water from water basins operates in the following manner.

The device is sunk by the rope 11 is the bottom of the water basin. While sinking the check valves 3 and 13 are opened and the device is throughly washed. The supports 9 are the first to reach the bottom, preventing the device from tipping. When the lower end of the coring tube 1 touches the bottom of a water basin, the bottom sediments begin to penetrate into the coring tube 1. The gradual filling of the coring tube 1 with the bottom sediments is accompanied by the simultaneous filling of the bathometer 12 with the bottom water through the check valve 3. The water previously contained in the bathometer 12 is forced out through the check valve 13. After the coring tube 1 has filled with the bottom sediments, the device is lifted by means of the rope 11, while the check valves 3 and 13 get closed. When the device is on land, the bolts 6 are screwed out and the coring tube 1 is released together with the bathometer 12. The bottom water contained in the bathometer 12 is released through the valve 15, with the valve 14 being open. Then the coring tube 1 is disassembled into separate sections in order to obtain the samples of bottom sediments in the form of thin layers.

The device according to the invention enables undisturbed sampling of bottom sediments in the form of separate layers, as well as of bottom water, being in direct contact with the bottom sediments. By selecting the height of the bathometer it is possible to take samples of bottom water of desirable layer thickness.

The invention has been described in detail with particular reference to preferred embodiments thereof, but it will be understood that variations and modifications can be effected within the spirit and scope of the invention.

What is claimed is:

1. A device for taking samples of bottom sediments and bottom water from water basins, comprising:
   at least one vertical coring tube;
   sections of said coring tube arranged in succession one after another longitudinally of said tube;
   a closed upper end of said tube;
   a check valve built in said upper end;
   an open lower end of said tube;
   a bathometer secured on said upper end of said tube;
   a lower end of said bathometer being at the same time the upper end of said tube;
   a closed upper end of said bathometer;
   a check valve built in said upper end of said bathometer;
   an upper part of said bathometer being distant from said upper end of said tube;
   a means in said upper part for intake of air;
   a lower part of said bathometer touching said upper end of said tube;
   a means in said lower part for release of water;
   a carrying element;
   said coring tube secured by its upper end to said carrying element.

2. A device according to claim 1, which includes at least three supports, each having upper and lower ends and each having a length exceeding the length of said coring tube, placed uniformly around said tube and secured by their upper ends to said carrying element.

* * * * *